US010387698B2

(12) United States Patent
Langerman et al.

(10) Patent No.: US 10,387,698 B2
(45) Date of Patent: Aug. 20, 2019

(54) READER APPARATUS FOR UPCONVERTING NANOPARTICLE INK PRINTED IMAGES

(71) Applicant: South Dakota Board of Regents, Pierre, SD (US)

(72) Inventors: David Langerman, Rapid City, SD (US); Jon Kellar, Rapid City, SD (US); William Cross, Rapid City, SD (US); P. Stanley May, Rapid City, SD (US); Julian Brackins, Rapid City, SD (US); Jeevan Meruga, Rapid City, SD (US); Aravind Baride, Rapid City, SD (US); John Rapp, Rapid City, SD (US)

(73) Assignee: SOUTH DAKOTA BOARD OF REGENTS, Pierre, SD (US)

( * ) Notice: Subject to any disclaimer, the term of this patent is extended or adjusted under 35 U.S.C. 154(b) by 0 days.

(21) Appl. No.: 15/552,486

(22) PCT Filed: Feb. 19, 2016

(86) PCT No.: PCT/US2016/018817
§ 371 (c)(1),
(2) Date: Aug. 21, 2017

(87) PCT Pub. No.: WO2016/134339
PCT Pub. Date: Aug. 25, 2016

(65) Prior Publication Data
US 2018/0046834 A1  Feb. 15, 2018

Related U.S. Application Data

(60) Provisional application No. 62/118,225, filed on Feb. 19, 2015.

(51) Int. Cl.
*G06K 7/10* (2006.01)
*C09D 11/50* (2014.01)
(Continued)

(52) U.S. Cl.
CPC ......... *G06K 7/10564* (2013.01); *B42D 25/29* (2014.10); *B42D 25/382* (2014.10);
(Continued)

(58) Field of Classification Search
CPC ................. G06K 7/10564; G06K 7/1417; C09D 11/50; C09D 11/03; C09D 11/037;
(Continued)

(56) References Cited

U.S. PATENT DOCUMENTS 6,158,659 A * 12/2000 Dickson ................. G02B 26/10
235/462.01
2005/0264001 A1  12/2005 Kerns et al.
(Continued)

FOREIGN PATENT DOCUMENTS

WO  2014140431 A1  9/2014

OTHER PUBLICATIONS

International Preliminary Report on Patentability for PCT/US16/18817, (dated Aug. 31, 2017).

*Primary Examiner* — Sonji N Johnson
(74) *Attorney, Agent, or Firm* — Goodhue, Coleman & Owens, P.C.

(57) ABSTRACT

An improved system and method for reading an upconversion response from nanoparticle inks is provided. A is adapted to direct a near-infrared excitation wavelength at a readable indicia, resulting in a near-infrared emission wavelength created by the upconverting nanoparticle inks. A short pass filter may filter the near-infrared excitation wavelength. A camera is in operable communication with the short pass filter and receives the near-infrared emission wavelength of the readable indicia. The system may further include an integrated circuit adapted to receive the near-infrared emission wavelength from the camera and generate a corresponding signal. A readable application may be in operable
(Continued)

communication with the integrated circuit. The readable application receives the corresponding signal, manipulates the signal, decodes the signal into an output, and displays and/or stores the output.

20 Claims, 7 Drawing Sheets

(51) Int. Cl.
  B42D 25/29       (2014.01)
  C09D 11/037      (2014.01)
  B42D 25/382      (2014.01)
  C09D 11/03       (2014.01)
  C09K 11/77       (2006.01)
  G06K 7/14        (2006.01)
  G01N 21/00       (2006.01)
  G07D 7/00        (2016.01)
  G01N 21/64       (2006.01)
  H01L 23/00       (2006.01)
(52) U.S. Cl.
  CPC ............ *C09D 11/03* (2013.01); *C09D 11/037* (2013.01); *C09D 11/50* (2013.01); *C09K 11/7766* (2013.01); *C09K 11/7783* (2013.01); *G01N 21/00* (2013.01); *G06K 7/1417* (2013.01); *G07D 7/00* (2013.01); *G01N 21/6456* (2013.01); *H01L 23/57* (2013.01)
(58) Field of Classification Search
  CPC ............ C09K 11/7783; C09K 11/7766; B42D 25/382; B42D 25/29; G07D 7/00; G01N 21/00; G01N 21/6456; H01L 23/57
  See application file for complete search history.

(56) References Cited

U.S. PATENT DOCUMENTS

| | | |
|---|---|---|
| 2009/0051027 A1 | 2/2009 | Lin |
| 2009/0122412 A1 | 5/2009 | Steenblik et al. |
| 2011/0318717 A1* | 12/2011 | Adamowicz ....... G09B 19/0092 434/127 |
| 2012/0212603 A1* | 8/2012 | Lindee ................ A22C 17/0033 348/89 |
| 2013/0087622 A1 | 4/2013 | Collins et al. |
| 2014/0261031 A1 | 9/2014 | Kellar et al. |

* cited by examiner

READER APPARATUS FOR UPCONVERTING NANOPARTICLE INK PRINTED IMAGES

STATEMENT REGARDING FEDERALLY FUNDED RESEARCH

This invention was made with government support under Grant Nos. EEC-1263343 and 1414211 awarded by the National Science Foundation (NSF).

FIELD OF THE DISCLOSURE

The present disclosure relates generally to detection of covert printing as enhanced security measures. More particularly, but not exclusively, the present disclosure relates to an apparatus, system and method for detecting and decoding near-infrared (NIR) luminescent images generated using upconverting nanoparticle (UCNP) inks.

BACKGROUND OF THE DISCLOSURE

Counterfeiting of goods is a major concern for corporate, federal and state organizations. Counterfeits can compromise the security, identity and value of products, documents, identifications, and currency, thereby exerting a strong negative impact on societal, financial and social wellbeing.

Of particular concern is document and image security. By their very nature, documents are susceptible to alteration and forgery. In particular, visual indicia printed on the document to establish the authenticity of the same may be modified or deleted by a malfeasant. In other instances, the details of and/or information contained within the document may be improperly altered to benefit a wrongdoer at the expense of another. Therefore, a need exists in the art to provide invisible taggants that can be read by a device to verify the authenticity of and/or information contained with a document. For example, artwork would benefit from having an associated taggant that is concealed and/or imperceptible to the naked eye, but readable by a device.

Of another particular concern is supply chain security and pharmaceutical packaging. An important component of supply chain security is screening and validating of the contents of cargo being shipped. Doing so often involves scanning and comparing barcodes, two-dimensional codes and/or radiofrequency identification (RFID) tags. Similarly, manufacturers and distributors of pharmaceuticals are increasingly investing in countermeasures, such as traceability and authentication technologies, to minimize the impact of counterfeit medicines deliberately mislabeled to deceive consumers. A savvy counterfeiter, however, may become privy to the location and properties of the identifiers of genuine packaging, products and/or pharmaceuticals and forge those as well. In order to reduce the cases of counterfeiting across supply chain management, pharmaceutical packing, and numerous additional industries, a need exists in the art for a scanning device capable of verifying critical product information encoded on covert and/or invisible taggants applied to packaging and/or products for authentication.

Of yet another particular concern is counterfeiting integrated circuits because of its potential to compromise the performance of a wide range of critical infrastructure ranging from healthcare devices to military equipment to space hardware. The counterfeit integrated circuits are often fraudulent or degraded products that have been either rejected during the quality control or recycled from waste. In operation, the counterfeiting of integrated circuits often involves removing a label of a casing by sanding, reprinting the label of a more expensive item, then selling it back to the manufacturer and/or a distributor for a profit.

The markings within the integrated circuit packaging can make tampering a difficult task without damaging the component itself or the electronic packaging. Integrated circuits are often enclosed in an epoxy case (or mold compound) and electronic circuit boards are frequently coated with polymer films. Epoxy is very chemically resistant and is insoluble in common solvents, making it difficult to remove in order to reach the embedded code. A system of markings coated below an opaque epoxy layer would be difficult to detect and quite tamper resistant. Therefore, a further need exists in the art to provide a device that can read and decode printed features through opaque, hard polymer or epoxy coatings.

Upconversion phosphors emit light at wavelengths shorter than that of the excitation light. The concentration and combination of lanthanide dopants influence both the wavelength and the intensity of the upconversion emission. The inks are a formulation of upconversion nanoparticles (UCNPs) dispersed in a polymer base. When used to print text or features (e.g., quick response (QR) codes) on paper, the upconversion ink is invisible to the eye under ambient conditions or ultraviolet excitation, but becomes visible upon excitation with NIR light. In particular, lanthanide-ion-doped $\beta$-NaYF$_4$ is recognized for exceptionally efficient visible upconversion upon excitation with NIR light with a wavelength of approximately 980 nanometers (nm). An exemplary system and method for creating NIR upconverting inks is disclosed by U.S. Pub. No. 2014/0261031 to Kellar et al., which is herein incorporated in its entirety.

$\beta$-NaYF$_4$ UCNPs doped with Yb$^{3+}$ and Tm$^{3+}$ are known for NIR-to-blue upconversion emission between wavelengths of 440 and 500 nm. These blue UCNP inks, however, also emit NIR light at a wavelength of 800 nm, which is invisible to the naked eye, but much more intense than the visible blue emission. Moreover, these coatings can be completely opaque as long as the coating transmits both 800 nm and 980 nm wavelengths. Therefore, a further need exists in the art to capture of NIR images of UCNP inks coated with NIR transparent materials that are opaque in the visible range.

SUMMARY

It is therefore a primary object, feature, and/or advantage of the present disclosure to improve on or overcome the deficiencies in the art. It is another object, feature, and/or advantage of the present disclosure to provide a device capable of capturing of NIR images of UCNP inks. The device may be used to verify covert taggants applied to products for authentication.

It is yet another object, feature, and/or advantage to provide strong security feature embeds information in the product and resists tampering, duplication or destruction without damaging the product integrity. The product may be an integrated circuit with an opaque epoxy packaging, under which the information could be disposed.

It is still another object, feature, and/or advantage of the present disclosure to provide a smart phone application capable of decoding upconverted QR codes or two-dimensional barcodes captured by a camera. The application will have the options to either scan and decode the QR code immediately, or to capture an image of the QR code and later decode the image within the application. The smartphone also control the infrared laser.

These and/or other objects, features, and advantages of the present disclosure will be apparent to those skilled in the art. The present disclosure is not to be limited to or by these objects, features and advantages. No single embodiment need provide each and every object, feature, or advantage.

According to an aspect of the disclosure, a system for reading an upconversion response from nanoparticle inks is provided. The system includes a readable indicia printed on a substrate. The readable indicia are printed with UCNP inks. A laser is in operable communication at the readable indicia. The laser directs a near-infrared excitation wavelength at the readable indicia, resulting in a near-infrared emission wavelength created by the UCNP inks. A short pass filter may be in operable communication with the readable indicia. The short pass filter receives the near-infrared excitation wavelength and the near-infrared emission wavelength, and filters the NIR excitation wavelength. The system also includes a camera in operable communication with the short pass filter. The camera collects the NIR emission wavelength of the readable indicia.

The system may further include an integrated circuit in electronic communication with the camera. The integrated circuit is adapted to receive NIR emission of the readable indicia from the camera and generate a corresponding signal. A readable application may be in operable communication with the integrated circuit. The readable application receives the corresponding signal, decodes the NIR emission of the readable indicia into an output, and displays the output.

According to another an aspect of the present disclosure, a method to read covert printed images includes the step of providing a readable indicia comprised of UCNP ink. The UCNP ink is excited with an NIR excitation wavelength generated by a laser. The NIR excitation wavelength is filtered with a short pass filter. An NIR emission wavelength of the readable indicia is collected with a camera.

The method may further include decoding the NIR emission wavelength of the readable indicia with an application to provide an associated output. The associated output is transmitted and displayed on a device. The NIR emission wavelength of the readable indicia may be manipulated to generate an altered image, after which the altered image is decoded.

BRIEF DESCRIPTION OF THE DRAWINGS

Illustrated embodiments of the disclosure are described in detail below with reference to the attached drawing figures, which are incorporated by reference herein, and where.

DETAILED DESCRIPTION OF THE PREFERRED EMBODIMENTS

Figure 1:
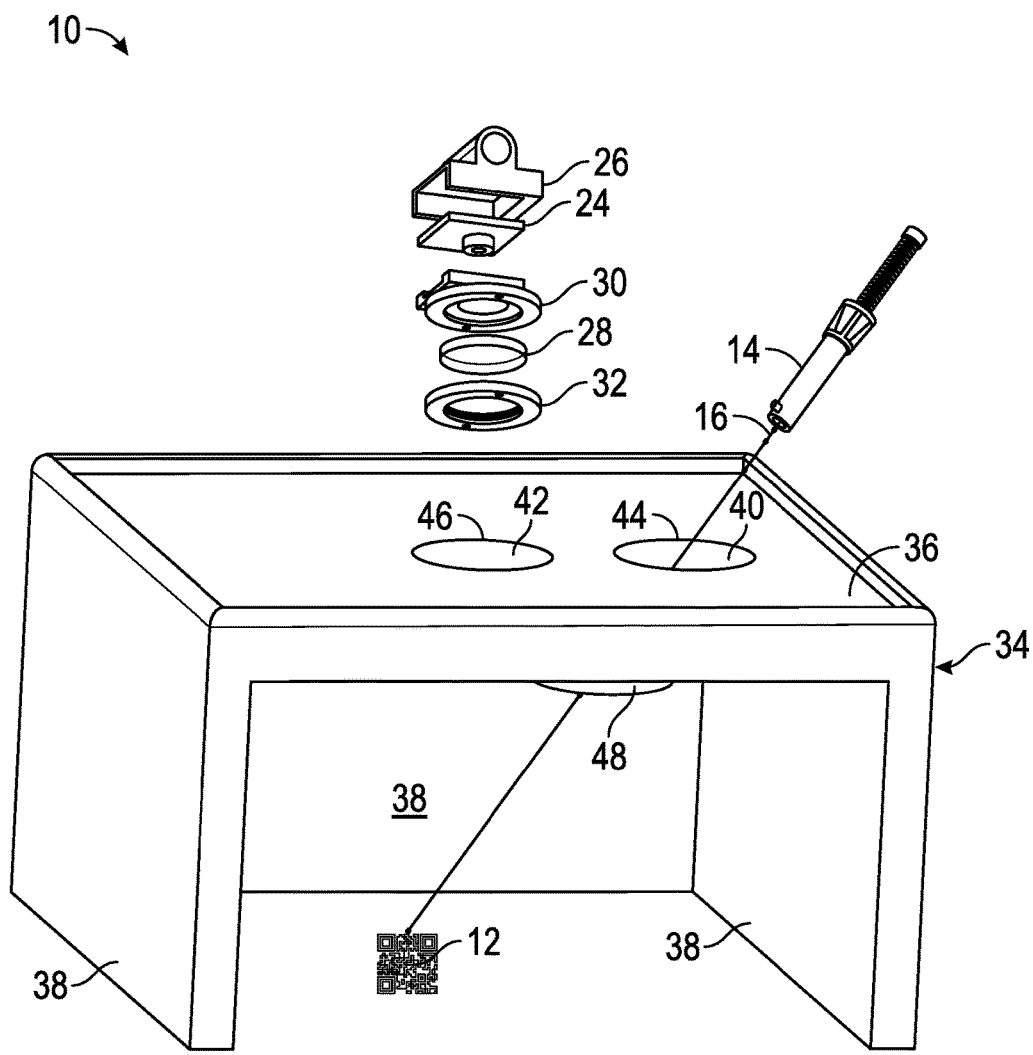
FIG. 1 is an exploded front perspective view of a reader apparatus in accordance with an illustrative embodiment.

Referring to FIG. 1, an exemplary detection and reading system 10 for covert readable indicia 12 of the present disclosure is illustrated. The system includes a laser 14 configured to produce an NIR excitation wavelength of light 16 directed at the readable indicia 12. In an exemplary embodiment, the NIR excitation wavelength is 980 25 nanometers (run), but other excitation wavelengths may be used without deviating from the objects of the present disclosure. For an excitation wavelength of 980 run, a representative model of the laser 14 is a Class IV Opto Engine LLC Model number MDL-N-980 nm-8 W laser. The laser 14, including the model above, may have variable power supply to permit a user and/or the system 10 to reduce wattage so as not to damage the substrate or the ink 30 of the readable indicia 12. In an alternate embodiment, the laser 14 may comprise a BIRP-0018 2.5 watt laser torch with a focusing feature, provided the power density is safe for use in the system 10. In yet another alternate embodiment, the laser 14 may comprise a 3 W 980 nm diode laser with focusing optics.

The inks of the present disclosure contain nanoparticles that have the unique property of emitting light at a lower wavelength than the excitation wavelength 16. Therefore, upon exposure to the excitation wavelength 16 produced by the laser 14, the UCNP ink of the readable indicia 12 generates an NIR reflected wavelength 18 and an NIR emission wavelength 20, as shown illustratively in FIG. 2. In particular, blue UCNP ink, not only upconverts the excitation wavelength 16 to a visible blue light 22, but also emits the NIR emission wavelength at 800 nm. An exemplary blue UCNP ink was formulated by dispersing oleic acid capped $\beta$-NaYF$_4$: 25% Yb$^{3+}$, 0.3% Tm$^{3+}$ nanoparticles in a solvent mixture of toluene/methyl benzoate (90:10 v/v) with Poly (methyl methacrylate) (PMMA). Another exemplary example includes a doping composition of 48% Yb$^{3+}$/2% Tm$^{3+}$. Yet another exemplary UCNP ink is comprised of 5 wt % of UCNPs were dispersed in the solvent mixture. In still yet another exemplary embodiment, a red-green-blue (ROB) system for full-color printing may be used with primary color red, green and blue upconversion inks activated with 10% Er$^{3+}$/2% Tm$^{3+}$, 17% Yb$^{3+}$/3% Er$^{3+}$ and 25% Yb$^{3+}$/0.3% Tm$^{3+}$ nanoparticles, respectively. The present disclosure contemplates utilizing any doping composition of Yb$^{3+}$/Tm$^{3+}$ that enhances the NIR emission wavelength of 800 nm.

Figure 2:
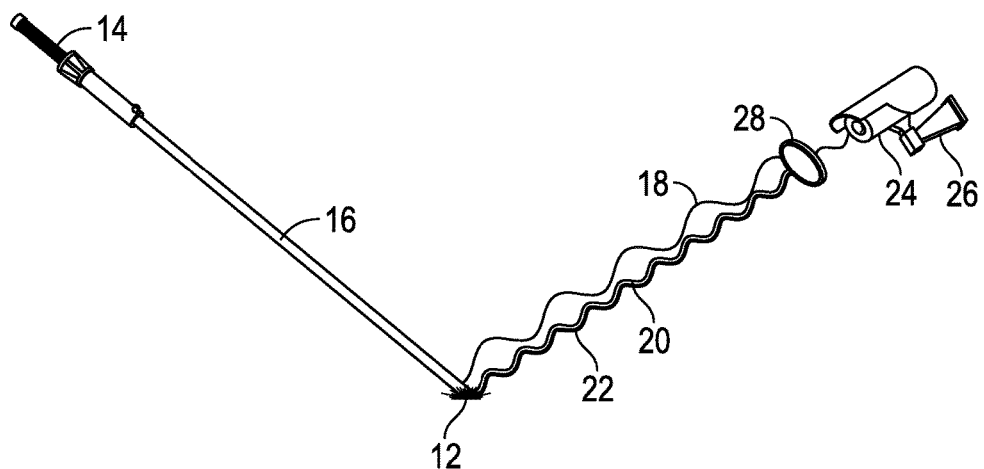
FIG. 2 is a front perspective view of a portion of the operation of a reader apparatus in accordance with an illustrative embodiment.

To capture the resulting image of the readable indicia 12, the system includes a camera 24, as shown illustratively in FIGS. 1 and 2. Representative models of the camera 24 may include Raspberry Pi NoIR or Microsoft VX-6000 webcam (with the infrared filter removed). The camera 24 may require connective means 26 to secure the camera 24 to a surface or other structure. In an embodiment illustrated in FIG. 5, the camera 24 is a stock camera on an Android (or iPhone) smartphone 27.

The system may also require a short pass filter 28 in operable communication with the camera 14, or more particularly within the sightline of the camera 14 such that the resulting image entering the camera 14 must pass through the short pass filter 28. In an alternative embodiment, an optical filter is designed into the camera. The short pass filter 28 ensures that the reflected wavelength 18 does not blind the camera 14 from detecting the emission wavelength 20. In an exemplary embodiment, a short pass filter model is 800 nm center wavelength (CWL), 25 millimeter diameter, Hard Coated OD4 50 nm Bandpass Filter from Edmund Optics. In an alternate embodiment, the optical filter is an 875 nm shortpass filter. As shown illustratively in FIG. 1, the short pass filter 28 may comprise a filter housing 30 and front ring 32.

Figure 3A:
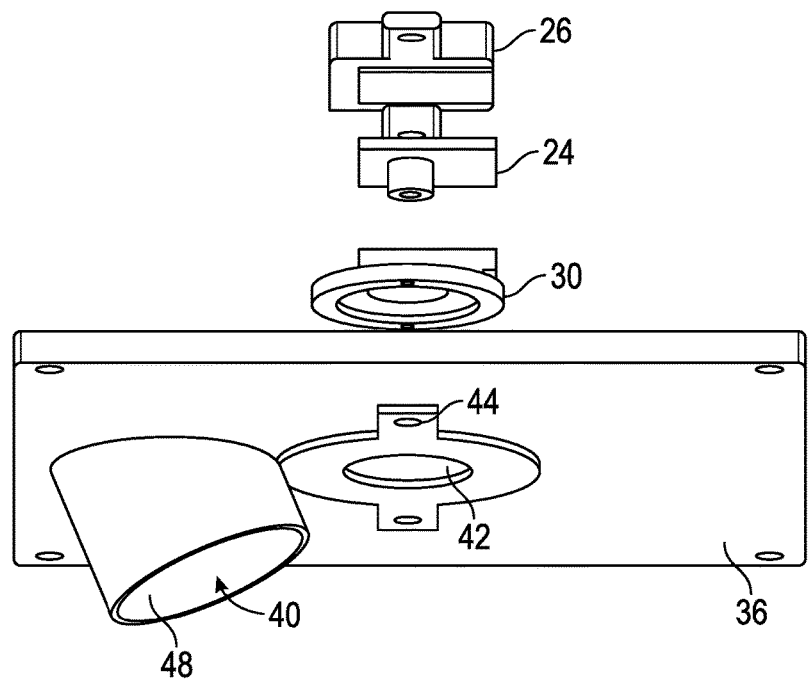
FIG. 3A is an exploded bottom perspective view of a reader apparatus in accordance with an illustrative embodiment.
Figure 3B:
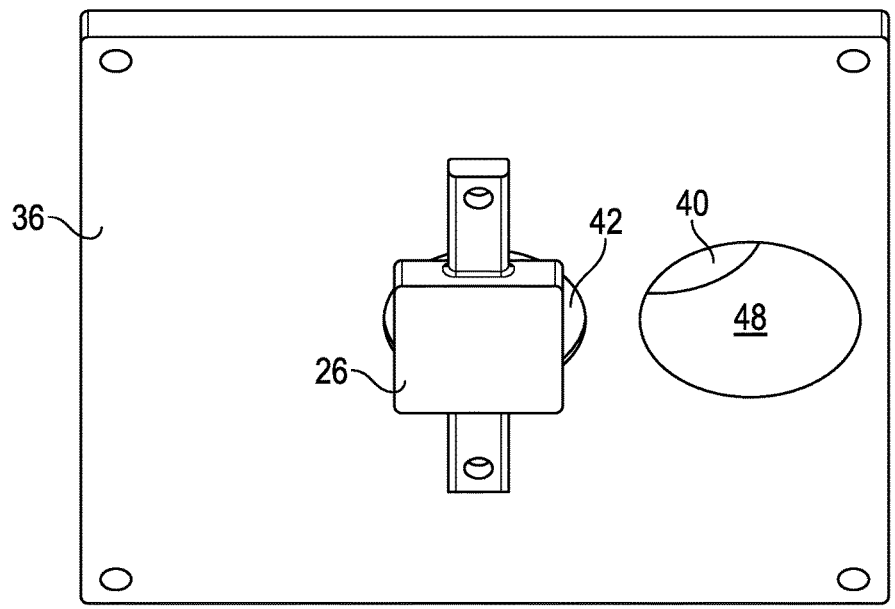
FIG. 3B is a tilted top plan view of a reader apparatus in accordance with an illustrative embodiment.
Figure 4A:
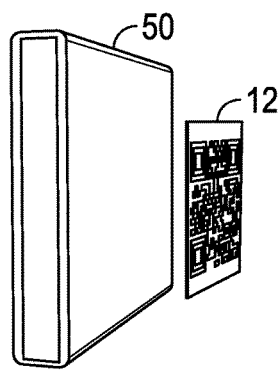
FIG. 4 is front perspective views of layered, covert QR codes in accordance with an illustrative embodiment.
Figure 4B:
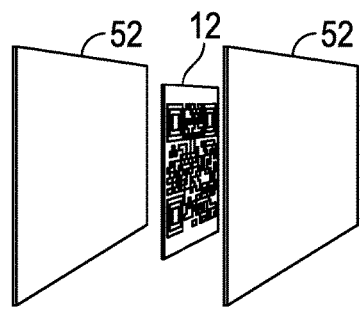
Figure 4C:
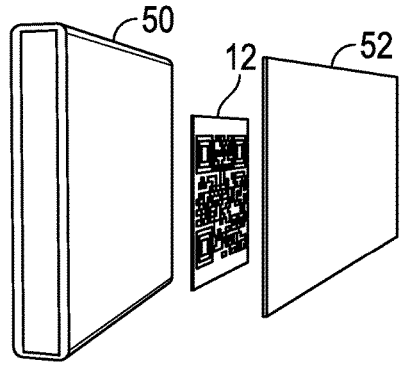
Figure 4D:
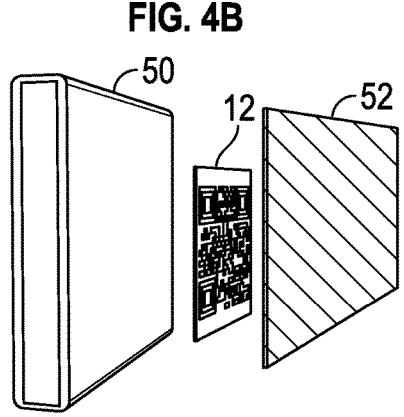

The system 10 may be installed on any suitable structure. In the illustrated embodiment of FIG. 1, the system is installed on a housing 34. The housing 34 may be constructed from any rigid material and through any manufacturing processes known in the art. In an exemplary embodiment, the housing 34 is three-dimensionally printed. In an alternate embodiment, the housing 34 is injection molded using thermosetting plastics. The housing 34 may comprise a top surface 36 and three or more side surfaces 38. In an exemplary embodiment, the top surface 36 comprised a length of eight inches and a width of four and one-half inches, but the present disclosure contemplates any combination of suitable dimensions. The housing 34 does not comprise a bottom surface, as a portion of the bottom of the housing 34 will be occupied by the readable indicia 12 during operation. The top surface 36 of the housing 34 may comprise two or more apertures 40 and 42. The first aperture 40 is adapted to permit the excitation wavelength 16 pass therethrough to the readable indicia. Similarly, the second aperture 42 is adapted to permit the reflected wavelength 18, the emission wavelength 20 and the visible blue light 22 to pass therethrough to the short pass filter 28 and the camera 14. The first aperture 40 and the second aperture 42 may also be associated a laser mount 44 and a camera mount 46, respectively, as shown illustratively in FIGS. 3A and 3B. A laser aperture tube 48 may extend inwardly into the housing 34 from the top surface 36.

Referring to FIG. 4, the readable indicia 12 may be disposed on a substrate 50 or a protective layer 52. The substrate 50 may be any surface or structure adapted to receive a readable indicia 12. In most instances, the substrate 50 will be a product. In an embodiment, the substrate 50 is an integrated circuit. As discussed in the present disclosure, of particular interest is providing for readable indicia 12 disposed between an integrated circuit and an epoxy, which may be illustrated by the opaque protective layer 52 of Sector D of FIG. 4. The NIR-to-NIR upconversion is advantageous because infrared light can penetrate many surfaces that visible light cannot. The UCNP inks, and more particularly blue UCNP inks, can be printed between the surface of the material and remain detectable by the system 10 of the present disclosure. Doing so offers additional advantages over bare prints or transparent protective layers 52. First, even if otherwise viewable intensities of visible emission are generated by the NIR excitation wavelength 16, the opaque protective layer 52 will block these wavelengths. Second, the invisibility of the latent print image on the uncoated substrate 50 is no longer a requirement. This permits the use of higher particle loadings or thicker print coatings, which, in turn, lower the threshold of power required to view and capture the image. Further, the use of opaque protective layers 52 deters tampering due to the unknown presence of the readable indicia 12 underneath.

In some instances, the opaque protective layer 52 may have fillers that compromise the NIR transmissive properties of the epoxy. Therefore, in an alternate embodiment, the opaque protective layer 52 may comprise a portion of the layer (e.g., "a window") of opaque epoxy without any filler that is transmissive of NIR in the wavelengths of 800 nm and 980 nm.

Figure 5:
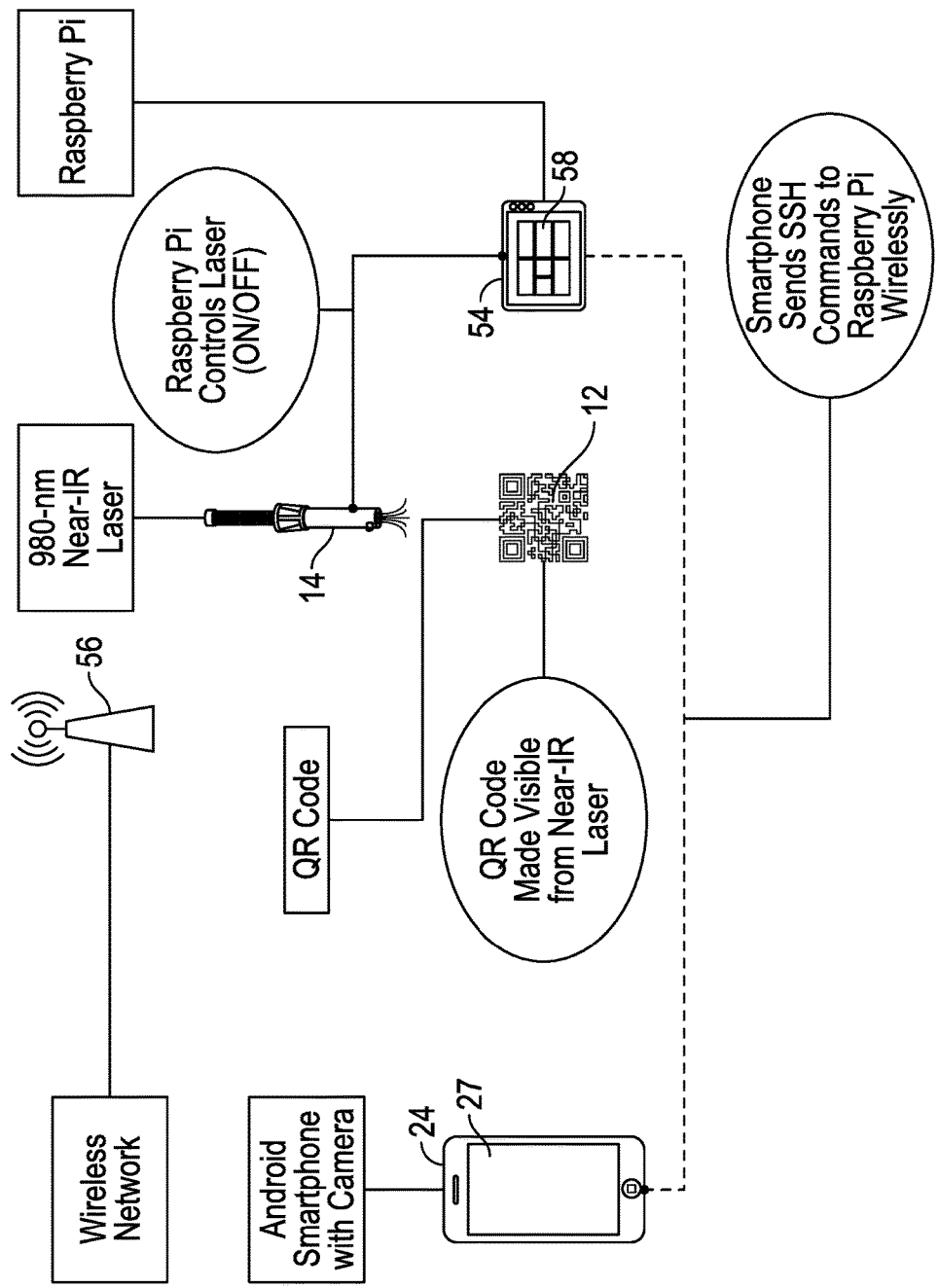
FIG. 5 is a schematic view of a reader apparatus system in accordance with an illustrative embodiment.

After the camera 24 captures an image of the readable indicia 12 consistent with the present disclosure, a signal may be transmitted to an integrated circuit 54 in operable communication with the camera 24, as shown illustratively in FIG. 5. The signal may be transmitted through a wired connection, or through any secure wireless network 56 commonly known in the art. In instances where a camera 24 is associated with a smartphone 27, the smartphone 27 may send secure shell (SSH) commands to the integrated circuit 54 through the wireless network 56. In an exemplary embodiment, the integrated circuit 54 may be a Raspberry Pi, Raspberry Pi Model B, or Raspberry Pi 2 board. In such an embodiment using a Raspberry Pi Model B board, the Raspberry Pi NoIR camera secures directly thereto. The smartphone 27 may also control the laser 14, as discussed in detail below. An alternative variable direct current (DC) power supply may also be integrated into the design for the smartphone reader application.

A user display 58 may be associated with the integrated circuit 54. The user display 58 can be controlled from the smartphone 27 through its connection to the Raspberry Pi. With the Raspberry Pi 2, the reading system may be controlled directly through the Raspberry Pi 2.

Figure 6:
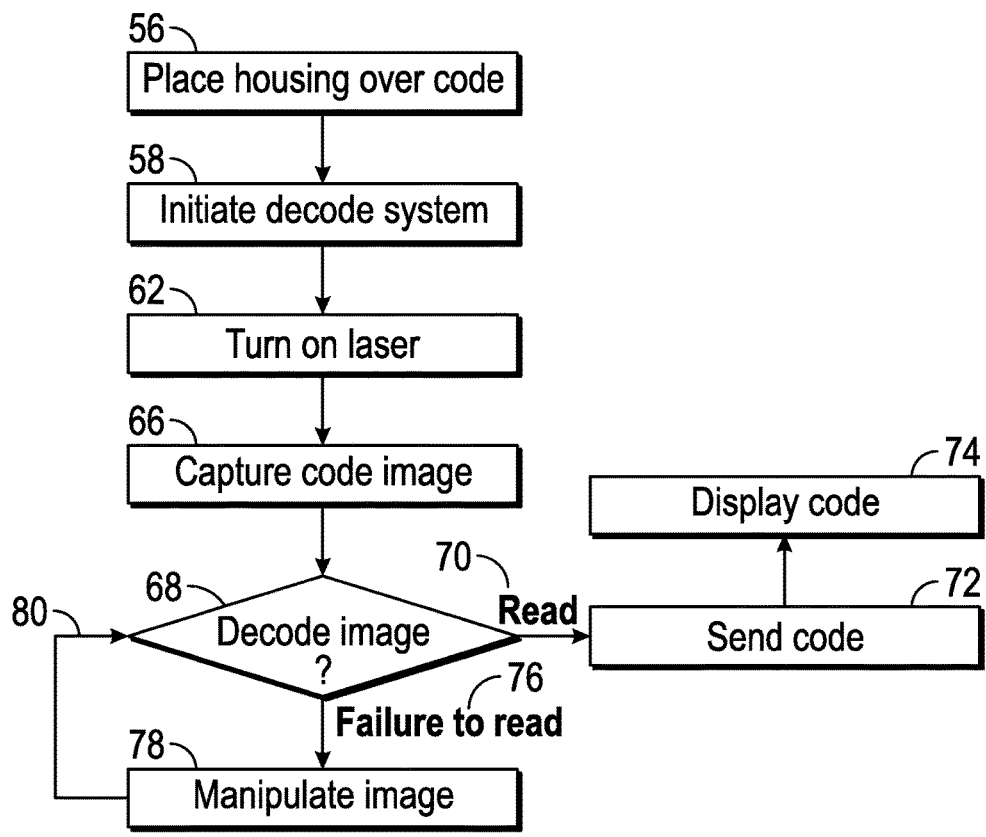
FIG. 6 is a schematic view of a method for decoding images printed with UCNP ink in accordance with an illustrative embodiment.
Figure 7:
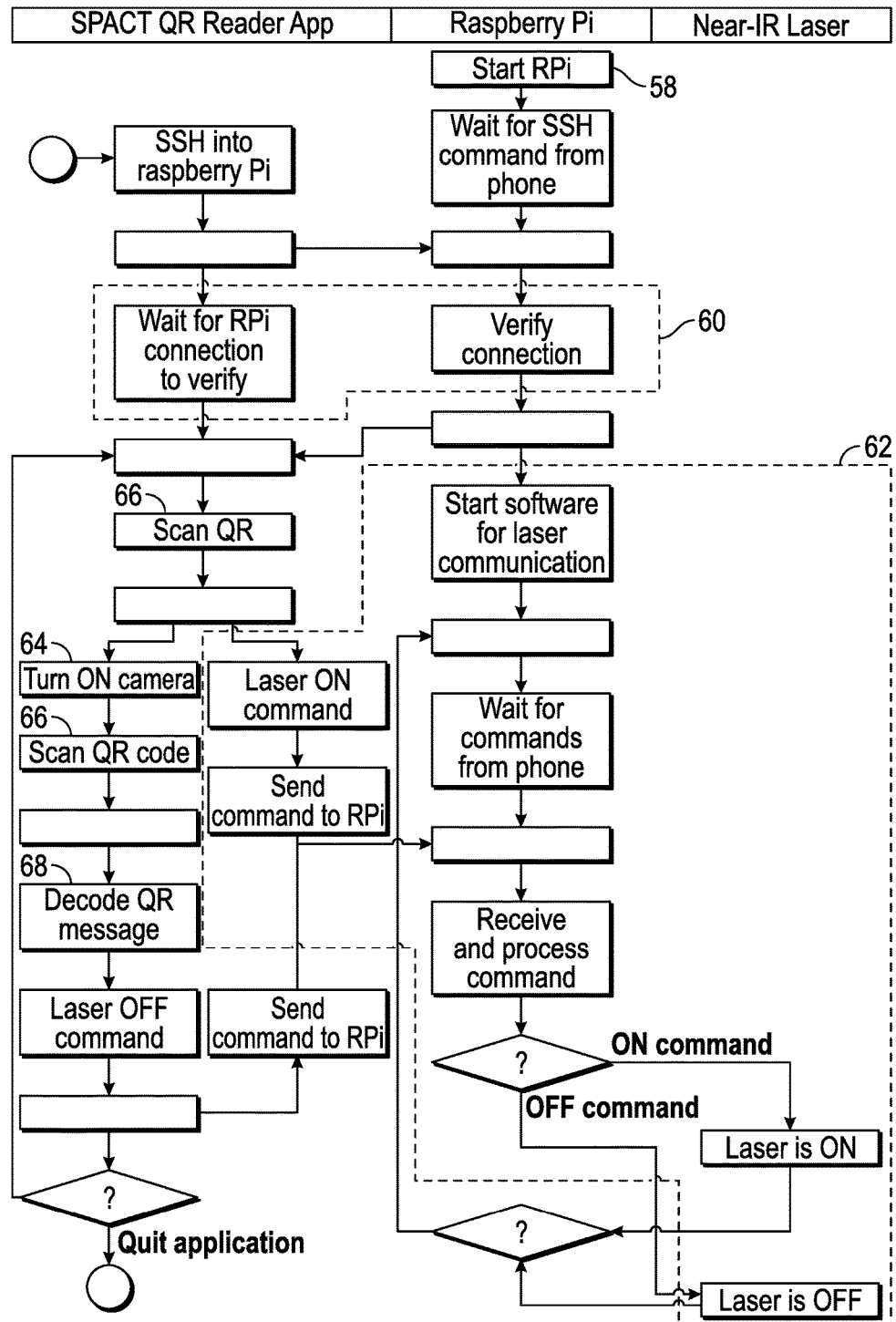
FIG. 7 is a schematic view of a method for decoding images printed with UCNP ink in accordance with an illustrative embodiment.

FIGS. 6 and 7 illustrate the operation of the system 10 and the integrated circuit 54. The housing 34 and/or the camera 24 is placed over 56 the readable indicia 12 such that the laser 14 will shine on the area with the readable indicia 12. The decoding system is activated 58, including starting the integrated circuit 54 such as Raspberry Pi. One the connection with the integrated circuit 58 is verified 60, the system 10 (or the integrated circuit 58) activates 62 the laser 14 and activates 64 the camera 24. In an exemplary embodiment, the Raspberry Pi is wired to a light emitting diode (LED), which can be turned on and off using the Raspberry Pi's General Purpose Input/Output (GPIO). A Python script accepting command arguments controls the GPIO and sends the appropriate commands to turn the LED on and off, which could be extended to the laser 14. An image is then captured 62 in accordance with the present disclosure discussed in detail above.

A decoding system is activated by the smartphone 27. The integrated circuit 54 collects the image attempts to decode the image/signal 68. The decoding system may comprise application software.

The software may be developed using an interface such as Eclipse IDE. In an embodiment using Eclipse IDE, the interface allows for packages and plug-ins to improve software development, such as GitHub integration for version control, Doxygen integration for documentation, and the Android Software Development Kit (SDK) for application development written in Java. The Android SDK allows software developers to create applications on the Android platform, with access to emulators and libraries required for Android application development. The present disclosure contemplates similar software developed for the iOS platform.

Figure 8:
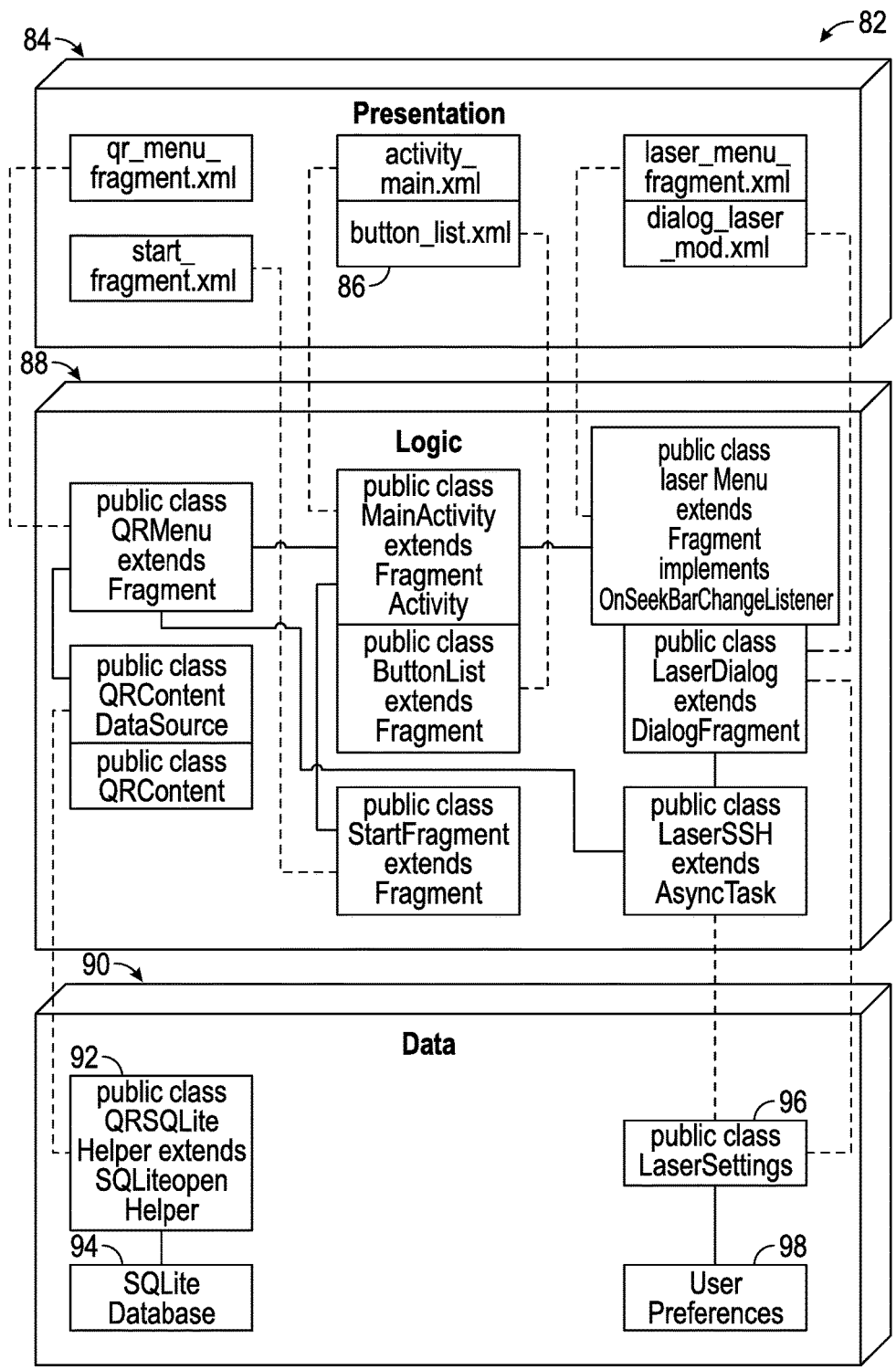
FIG. 8 is a schematic view of components of a reader application for decoding images printed with UCNP ink in accordance with an illustrative embodiment.

Referring to FIG. 8, the architecture of the reader application 82 can be broken into three main components, as shown illustratively in FIG. 8. The presentation layer 84 consists of the layout, or .XML files, of the application. These files dictate the appearance of the reader application 82 and define the interface objects in the application, such as buttons 86 and images of the various fragments. The logic layer 88 consists of Java files that dictate the behavior of the application. The foreground of the logic layer 88 contains the Java files that directly correspond to the layout files and describe the behavior of all objects created in the .XML files. The background of the logic layer contains the classes that describe the behavior of the database interactions in the application, and the behavior of the laser interactions in the application. The data layer 90 consists of Java files that directly access data stored within the application. For example, the QRSQLiteHelper class 92 interacts with the SQL Database 94 for storing QR code results in a database on the smartphone 27. The LaserSettings class 96 accesses User Preferences 98 stored in the reader application in order to remember the settings used to connect to an NIR laser 14 through an internet connection.

Returning to FIGS. 6 and 7, if the image/signal is read and/or decoded 70, the decoded data is sent 72 to the smartphone 27 to be displayed 74. The decoded data may also be stored. If the image/signal cannot be correctly decoded 76, image manipulation may occur 78. The image manipulation protocol may be automatic or manual. In an exemplary embodiment, the typical manipulation steps include, but are not limited to, cropping, centering. straightening, turning colors to grayscale, pixilation, altering contrast and brightness, inverting the color display (i.e., black become white and white becomes black), thresholding to reduce noise, retouching the finder code areas and sharpening the image. After any image manipulation 78, the step of decoding the image/signal 68 is repeated. The steps of image manipulation 78 and decoding the image/signal 68 may be repeated as many times as necessary to produce decoded signal or otherwise cancelled by the user. The decoded signal may be compared against databases for product verification and authenticity.

In an exemplary embodiment, the application will have the option to capture the image and decode the signal immediately, or to capture the image and later decode the image within the application. Further, the smartphone 27 and application software permits a user to access to various camera settings while scanning, such as aperture, exposure, focus, and the like.

The disclosure is not to be limited to the particular embodiments described herein. In particular, the disclosure contemplates numerous variations in the type of ways in which embodiments of the disclosure may be applied a device, system and/or method for detecting and decoding NIR luminescent images generated using UCNP inks. In addition to the security printing applications discussed herein, NIR-to-NIR UCNP inks may be applied in bio-imaging, because both the excitation and emission (800 nm) wavelengths fall within the biological transparency window. Therefore, emission wavelength of 800 nm from UCNP inks loaded into biological tissue can be imaged by an NIR exciting wavelength of 980 nm. The foregoing description has been presented for purposes of illustration and description. It is not intended to be an exhaustive list or limit any of the disclosure to the precise forms disclosed. It is contemplated that other alternatives or exemplary aspects that are considered included in the disclosure. The description is merely examples of embodiments, processes or methods of the disclosure. It is understood that any other modifications, substitutions, and/or additions may be made, which are within the intended spirit and scope of the disclosure. For the foregoing, it may be seen that the disclosure accomplishes at least all that is intended.

The previous detailed description is of a small number of embodiments for implementing the disclosure and is not intended to be limiting in scope. The following claims set forth a number of the embodiments of the disclosure with greater particularity.

What is claimed is:

1. A system to read an upconversion response from nanoparticle inks, the system comprising
   a readable indicia printed on a substrate, the readable indicia being printed with upconverting nanoparticle inks;
   a housing having a top surface and one or more supporting surfaces to the top surface, at least two or more apertures in the top surface of the housing, a first aperture of the at least two or more apertures and a second aperture of the at least two or more apertures disposed apart in the top surface of the housing;
   a laser operably attached at the first aperture in operable communication with the readable indicia, wherein a near-infrared excitation wavelength is directed from the laser at the readable indicia;
   a near-infrared emission wavelength created by the upconverting nanoparticle inks;
   a short pass filter in operable communication with the readable indicia, the short pass filter adapted to receive the near-infrared excitation wavelength, receive the near-infrared emission wavelength, and to filter the near-infrared excitation wavelength; and
   a camera operably attached at the second aperture with an optical lens of the camera in operable communication with the short pass filter, wherein the near-infrared emission wavelength is collected through the optical lens from the short pass filter.

2. The system of claim 1 further comprising:
   an integrated circuit in electronic communication with the camera, wherein the near-infrared emission wavelength of the readable indicia is received by the integrated circuit from the camera and wherein the integrated circuit generates a corresponding signal;
   a reader application in operable communication with the integrated circuit, the reader application adapted to:
   (a) receive the corresponding signal from the integrated circuit;
   (b) decode the signal into an output; and
   (c) display the output.

3. The system of claim 2 wherein the output is displayed on a smartphone.

4. The system of claim 2 wherein the signal is manipulated by the application.

5. The system of claim 1 further comprising:
   a housing connected to the laser, the short pass filter, and the camera;
   a first aperture in the housing through which the camera receives the near-infrared emission wavelength of the readable indicia;
   a second aperture in the housing through which the laser produces the near-infrared excitation wavelength.

6. The system of claim 1 wherein the readable indicia is a quick-response code reader.

7. The system of claim 1 wherein the substrate is an integrated circuit chip, wherein an epoxy is disposed on the integrated circuit chip and covers the readable indicia.

8. The system of claim 6 wherein the epoxy further comprises a portion of opaque epoxy having one or more fillers compromising transmission properties of the epoxy and a portion of transmissive epoxy resin, wherein the readable indicia is disposed below the portion of transmissive epoxy resin.

9. The system of claim 1 wherein the near-infrared excitation wavelength is 980 nanometers.

10. The system of claim 1 wherein the near-infrared emission wavelength is 800 nanometers.

11. The system of claim 1 wherein the upconverting nanoparticle inks are blue upconverting nanoparticle inks.

12. The system of claim 1 wherein the upconverting nanoparticle inks are comprised of oleic acid capped —$NaYF_4$, 25% $Yb^{3+}$, 0.3% $Tm^{3+}$ nanoparticles in a solvent mixture of toluene/methyl benzoate (90:10 v/v) with Poly (methyl methacrylate).

13. The system of claim 12 wherein the upconverting nanoparticle inks are comprised of a doping composition of 48% $Yb^{3+}$/2% $Tm^{3+}$.

14. A method to read covert printed images, the method comprising the steps of:
providing a readable indicia comprised of upconverting nanoparticle ink;
exciting the upconverting nanoparticle ink with a near-infrared excitation wavelength generated by a laser;
filtering the near-infrared excitation wavelength with a short pass filter; and collecting a near-infrared emission wavelength of the readable indicia from the short pass filter through the optical lens of a camera;
decoding the near-infrared emission wavelength from the readable indicia with a reader application, wherein processing comprises:
a processing architecture having a presentation layer providing an appearance on the reader application with one or more buttons and images of fragments from the near-infrared emission wavelength;
a logic layer having one or more executable files providing control of the reader application by storing and retrieving stored objects from a database of stored objects and one or more laser interactions from the near-infrared emission wavelength; and
a data layer having an executable file for accessing data stored in the reader application.

15. The method of claim 14 further comprising the steps of:
providing an output from decoding the near-infrared emission wavelength of the readable indicia with the reader application;
transmitting the associated output to a device; and displaying the associated output on the device.

16. The method of claim 15 further comprising the step of:
manipulating the near-infrared emission wavelength of the readable indicia to generate an altered image; and decoding the altered image.

17. The method of claim 14 wherein the upconverting nanoparticle ink is blue upconverting nanoparticle ink.

18. The method of claim 14 wherein the near-infrared excitation wavelength is 980 nanometers.

19. The method of claim 14 wherein near-infrared emission wavelength is 800 nanometers.

20. The method of claim 14 wherein the upconverting nanoparticle inks are comprised of a doping composition of 48% $Yb^{3+}$/2% $Tm^{3+}$.

* * * * *